United States Patent
Gia et al.

(10) Patent No.: US 6,589,230 B2
(45) Date of Patent: *Jul. 8, 2003

(54) SYSTEM FOR DETACHING AN OCCLUSIVE DEVICE WITHIN A MAMMALIAN BODY USING A SOLDERLESS, ELECTROLYTICALLY SEVERABLE JOINT

(75) Inventors: Son Gia, San Jose, CA (US); Hong Doan, Santa Clara, CA (US); Pete Phong Pham, Fremont, CA (US); Ivan Sepetka, Los Altos, CA (US); U. Hiram Chee, San Carlos, CA (US); Michael Mariant, San Jose, CA (US); David Kupiecki, San Francisco, CA (US)

(73) Assignee: Target Therapeutics, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/428,297

(22) Filed: Oct. 27, 1999

(65) Prior Publication Data

US 2001/0049521 A1 Dec. 6, 2001

Related U.S. Application Data

(60) Continuation of application No. 08/743,494, filed on Nov. 4, 1996, now Pat. No. 6,123,714, which is a continuation of application No. 08/485,502, filed on Jun. 7, 1995, now abandoned, which is a division of application No. 08/367,061, filed on Dec. 30, 1994, now abandoned.

(51) Int. Cl.[7] .............................................. A61B 17/00
(52) U.S. Cl. ........................ 606/1; 606/151; 606/213; 606/200; 606/108
(58) Field of Search .............................. 606/108, 151, 606/191–200, 1, 127, 213; 604/507, 508, 510, 517, 52, 164, 13, 523–539; 623/1.1, 2.1, 2.11, 11.11, 66.1, 900, 902–904

(56) References Cited

U.S. PATENT DOCUMENTS

| | | | |
|---|---|---|---|
| 3,868,956 A | | 3/1975 | Alfidi et al. |
| 4,739,768 A | | 4/1988 | Engleson |
| 4,884,579 A | | 12/1989 | Engleson |
| 4,994,069 A | | 2/1991 | Ritchart et al. |
| 5,108,407 A | | 4/1992 | Geremia et al. |
| 5,122,136 A | | 6/1992 | Guglielmi et al. |
| 5,226,911 A | | 7/1993 | Chee et al. |
| 5,234,003 A | * | 8/1993 | hall ........................ 600/585 |
| 5,250,071 A | | 10/1993 | Palermo |
| 5,353,808 A | * | 10/1994 | viera ........................ 600/585 |
| 5,354,295 A | | 10/1994 | Guglielmi et al. |
| 5,382,259 A | | 1/1995 | Phelps et al. |
| 5,423,829 A | | 6/1995 | Pham et al. |
| 5,891,128 A | | 4/1999 | Gia et al. |
| 6,123,714 A | * | 9/2000 | Gia et al. ................ 606/151 |

FOREIGN PATENT DOCUMENTS

| | | |
|---|---|---|
| WO | WO 94/16632 | 8/1994 |
| WO | WO 95/12367 | 5/1995 |

* cited by examiner

*Primary Examiner*—Glenn K. Dawson
(74) *Attorney, Agent, or Firm*—Bingham McCutchen LLP

(57) ABSTRACT

A solderless sacrificial link between a detachable member which is placed at and is intended to remain at a desired site within the mammalian body and the core wire used to introduce the detachable member. The detachable member device may be one used to create emboli in the vascular system or may be of any other type deliverable into the human body and detached into an ionic aqueous environment, either for later removal or permanent placement.

8 Claims, 5 Drawing Sheets

SYSTEM FOR DETACHING AN OCCLUSIVE DEVICE WITHIN A MAMMALIAN BODY USING A SOLDERLESS, ELECTROLYTICALLY SEVERABLE JOINT

CROSS-REFERENCE TO RELATED APPLICATIONS

This application is a continuation of U.S. patent application Ser. No. 08/743,494, filed Nov. 4, 1996, now U.S. Pat. No. 6,123,714, which is a continuation of U.S. patent application Ser. No. 08/485,502, filed Jun. 7, 1995, now abandoned, which in turn is a divisional of U.S. patent application Ser. No. 08/367,061, filed Dec. 30, 1994, now abandoned, the entirety of which are hereby incorporated by reference.

FIELD OF THE INVENTION

This invention is an apparatus primarily used for endovascular occlusion through the formation of thrombi in arteries, veins, aneurysms, vascular malformations, and arteriovenous fistulas. In particular, it deals with a solderless sacrificial link between a detachable device which is introduced to and is intended to remain at the desired site within the body and the core wire used to introduce the detachable device. The detachable device may be one used to create emboli in the vascular system or may be of any other type deliverable into the human body and detached into an ionic aqueous environment, either for later removal or permanent placement.

BACKGROUND OF THE INVENTION

Approximately 25,000 intracranial aneurysms rupture each year in North America. The primary purpose of treatment for a ruptured intracranial aneurysm is to prevent rebleeding. There are a variety of ways to treat ruptured and non-ruptured aneurysms. Possibly the most widely known of these procedures is an extravascular approach using surgery or microsurgery. This treatment is common with intracranial berry aneurysms. The method comprises a step of clipping the neck of the aneurysm, performing a suture ligation of the neck, or wrapping the entire aneurysm. Each of these procedures is formed by intrusive invasion into the body and performed from the outside of the aneurysm or target site. General anesthesia, craniotomy, brain retraction, and placement of a clip around the neck of the aneurysm are typically required in these surgical procedures. The surgical procedure is often delayed while waiting for the patient to stabilize medically. For this reason, many patients die from the underlying disease or defect prior to the initiation of the procedure.

Another procedure—the extra-intravascular approach—involves surgically exposing or stereotactically reaching an aneurysm with a probe. The wall of the aneurysm is then perforated from the outside and various techniques are used to occlude the interior in order to prevent it from rebleeding. The techniques used to occlude the aneurysm include electrothrombosis, adhesive embolization, hog hair embolization, and ferromagnetic thrombosis. These procedures are discussed in U.S. Pat. No. 5,122,136 to Guglielmi et al., the entirety of which is incorporated by notice.

A still further approach is the least invasive and is additionally described in Guglielmi et al. It is the endovascular approach. In this approach, the interior of the aneurysm is entered by use of a catheter such as those shown in Engelson (Catheter Guidewire), U.S. Pat. No. 4,884,579 and also in Engelson (Catheter for Guidewire Tracking), U.S. Pat. No. 4,739,768. These patents describe devices utilizing guidewires and catheters which allow access to the aneurysm from remote portions of the body. Specifically by the use of catheters having very flexible distal regions and guidewires which are steerable to the region of the aneurysm, embolic devices which may be delivered through the catheter are an alternative to the extravascular and extra-intravascular approaches.

The endovascular approach typically includes two major steps. The first step involves the introduction of the catheter to the aneurysm site using devices such as shown in the Engelson patents. The second step often involves filling the aneurysm in some fashion or another. For instance, a balloon may be introduced into the aneurysm from the distal portion of the catheter where it is inflated, detached, and left to occlude the aneurysm. In this way, the parent artery is preserved. Balloons are becoming less in favor because of the difficulty in introducing the balloon into the aneurysm sac, the possibility of an aneurysm rupture due to overinflation of the balloon within the aneurysm, and the risk associated with the traction produced when detaching the balloon.

A highly desirable embolism-forming device which may be introduced into an aneurysm using endovascular placement procedures, is found in U.S. Pat. No. 4,994,069, to Ritchart et al. There is described a device—typically a platinum/tungsten alloy coil having a very small diameter—which may be introduced into an aneurysm through a catheter such as those described in Engelson above. These coils are often made of wire having a diameter of 2–6 mils. The coil diameter may be 10–30 mils. These soft, flexible coils may be of any length desirable and appropriate for the site to be occluded. For instance, the coils may be used to fill a berry aneurysm. Within a short period of time after the filling of the aneurysm with the embolic device, a thrombus forms in the aneurysm and is shortly thereafter complemented with a collagenous material which significantly lessens the potential for aneurysm rupture. Coils such as seen in Ritchart et al. may be delivered to the vasculature site in a variety of ways including, e.g., mechanically detaching them from the delivery device as is shown in U.S. Pat. No. 5,250,071, to Palermo or by electrolytic detachment as is shown in Guglielmi et al. (U.S. Pat. No. 5,122,136) as was discussed above.

Guglielmi et al. shows an embolism-forming device and procedure for using that device. Specifically, Guglielmi et al. fills a vascular cavity such as an aneurysm with an embolic device such as a platinum coil which coil has been endovascularly delivered. The coil is then severed from its insertion tool by the application of a small electric current. Desirably, the insertion device involves a guidewire which is attached at its distal end to an embolic device by an electrolytic, sacrificial joint. Guglielmi et al. suggests that when the embolic device is a platinum coil, the platinum coil may be 1–50 cm. or longer as is necessary. Proximal of the embolic coil is a guidewire, often stainless steel in construction. The guidewire is used to push the platinum embolic coil, obviously with great gentleness, into the vascular site to be occluded. The patent shows a variety ways of linking the embolic coil to the pusher guidewire. For instance, the guidewire is tapered at its distal end and the distal tip of the guidewire is soldered into the proximal end of the embolic coil. Additionally, a stainless steel coil is wrapped coaxially about the distal tapered portion of the guidewire to provide column strength to the guidewire. This coaxial stainless steel wire is joined both to the guidewire and to the embolic coil.

Insulation may be used to cover a portion of the strength-providing stainless steel coil. This arrangement provides for two regions which must be electrolytically severed before the embolic coil is severed from the guidewire.

A further variation of the Guglielmi Detachable Coil is one in which the distal tip of the stainless steel guidewire is not soldered to the proximal end of the embolic device. A simple conical stainless steel wire is included from the stainless steel guidewire to the embolic coil.

A further variation found in Guglielmi et al. includes a thin, threadlike extension between the guidewire core and the proximal end of the embolic coil. In this way, the guidewire does not extend to the embolic coil, but instead relies upon a separately introduced extension.

A continuation-in-part of the Guglielmi et al patent discussed above filed on Feb. 24, 1992 entitled "[IMPROVEMENTS] IN AN ENDOVASCULAR ELECTROLYTICALLY DETACHABLE WIRE AND TIP FOR THE FORMATION OF THROMBUS IN ARTERIES, VEINS, ANEURYSMS, VASCULAR MALFORMATIONS AND ARTERIOVENOUS FISTULAS" now U.S. Pat. No. 5,354,295 issued Oct. 11, 1994 describes the use of mechanically detachable embolic devices as well as those which are electrolytically detachable. The embolic devices may be augmented with attached filaments.

Dr. Taki has devised a variation of the Guglielmi detachable coil using a copper link between the guidewire and the coil.

None of the noted procedures using electrolytically detachable embolic devices suggests the concept of eliminating the solder in the sacrificial link, specifically by crimping and welding the detachable device to the associated pusher. This permits clean detachment of the embolic device in a facile and quick fashion.

SUMMARY OF THE INVENTION

As noted above, this invention is a joint which is severable by electrolysis in an aqueous environment within the human or mammal body. It may be used in combination with a member which is placed into the body either via creation of an artificial opening, e.g., by introduction into the vasculature, or by use of a normally existing opening, e.g., by placement in the genito-urinary tract. The member so-placed may either remain in place or may be later removed. The preferred device is one in combination with an embolus-forming member for forming a vascular occlusion at a selected site. Generally, the preferred device comprises a guidewire, or core wire, having a distal tip which distal tip may be introduced into the selected vascular site or cavity. The core wire is joined to the distal tip or embolic device in such a way that the vascular device may be electrolytically detached by application of a current to the core or guidewire. The improvement to the preferred variation involves the use of a specifically formed, discrete, sacrificial link between the core wire and the vascular device to allow clean and quick detachment from the core wire. The focussed electrolysis found at the sacrificial site provides a clean severed joint and a predictable time for electrolysis.

There are several variations of the sacrificial joint each, however, involving a solderless, usually crimped and welded, joint between the core wire and the detachable member.

DESCRIPTION OF THE INVENTION

Each of the discrete sacrificial joints discussed below may be used in the device shown in U.S. Pat. No. 5,122,136 to Guglielmi et al., the entirety of which patent is incorporated by reference.

It should be pointed out that one of the major benefits in using the solderless joints specified in this application is the predictability for time of detachment provided due to the absence of solder. Solder, it turns out, often provides a significant unknown in predicting the time for detachment. Solders are not altogether uniform in their concentration once they have cooled and occasionally will create spots of higher potential electrolytic activity because of a higher concentration of a particular metal in the cooled solder flow. Additionally, the fluxes that must be used with such solders may inadvertently be included as aberrations within the surface of the solder and cause anomalies in the electrolytic degradation. Finally, the solder itself will electrolytically degrade at a rate different than that of the sacrificial link. Elimination of the solder and use of a simpler cast of materials renders the predictability of electrolytic detachment much more consistent.

Figure 1:
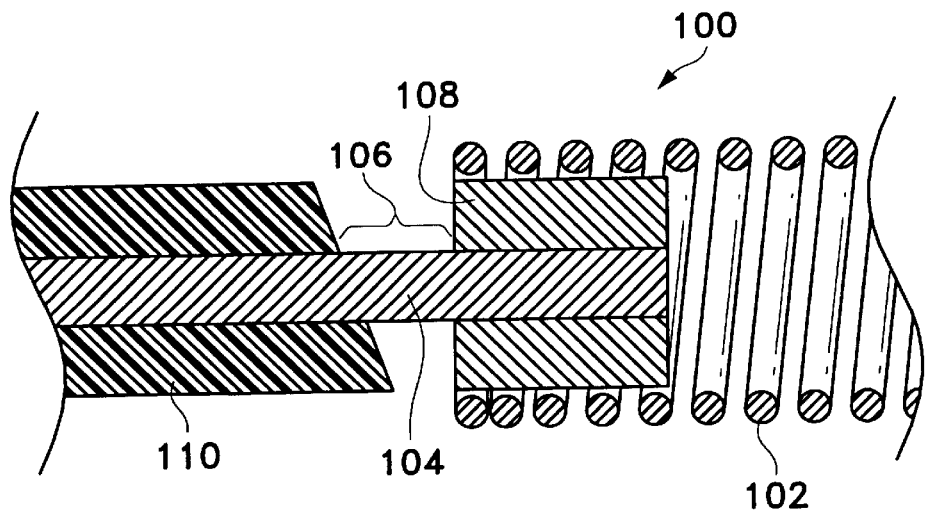
FIGS. 1–7 show sideview, partial cross-sectional views of variations of the inventive, electrolytically susceptible, sacrificial link between a core wire and an embolic device.

FIG. 1 shows the details of the electrolytic joint 100. Specifically, shown in highly magnified cross-section is a detachable electrolytic device 102, in this case a coil. The detachable embolic device 102 is of a material higher in the electromotive series than the material making up the core wire 104 and, in particular, the area of the core wire 104 which is to be dissolved (106). For instance, embolic coil 102 may be of a material such as platinum or other noble metal, and the sacrificial area 106 may be of steel, stainless steel, nickel, nickel/titanium alloys, or other materials which will electrolytically dissolve in an aqueous fluid medium such as blood, saline solution, or other bodily fluid prior to the dissolution of detachable device 102. The embolic device 102 in this stylized FIG. 1 is placed upon a sleeve 108 which is also of a material more noble than is the material found in the core wire 104. The remainder of core wire 104 is covered in some fashion by an insulator 110. The length of the exposed electrolytic dissolution area 106 is quite short. For instance, it may be as short as 0.010 inches, and typically is no longer than 0.150 inches in length.

The sleeve 108 need not be of the same material as is the detachable device or member 102. It simply requires that the sleeve 108 not decompose prior to core wire 104. Suitable solder-less attachment methods for the sleeve 108 include crimping the sleeve onto the distal end of core wire 104, welding the sleeve 108 onto the core wire 104, screwing one into the other, or a combination of the steps. Obviously, other solderless methods will be apparent to the skilled worker after review of the disclosure herein. Further, the detachable device 102 is desirably welded onto the outer surface of the sleeve 108 but may be crimped thereto.

The core wire 104 is covered with appropriate insulating material. These insulating materials may be made of materials such as polytetrafluoroethylene or other fluoropolymers (Teflon7), polyurethane, parylene, polyethylene, polypropylene, polyethylene terephthalate (PET), or other known suitable, typically polymeric, material. It is within the scope of this invention that the insulating material may equivalently be a coating of more noble metals, such as gold or the like. This equivalent layer may be plated or otherwise placed onto the core wire 104. Again, it is the intent of this invention that the sacrificial area 106 be narrowly outlined so that a small, discrete area of the core wire is exposed to the surrounding fluid for electrolytic dissolution. It is also quite highly desirable that the area proposed for electrolytic dissolution be of a single dissolvable material completed clean of other electrolyzable materials. We have also found it desirable to coat the electrolyzable area with one or more of the noted polymers, particularly parylene, and remove a selected area by the use of an appropriately high energy laser beam.

Figure 2:
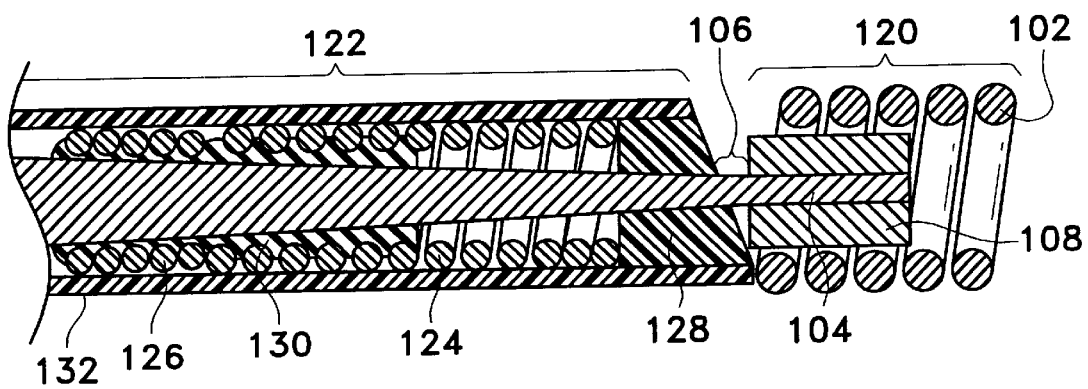
Figure 3:
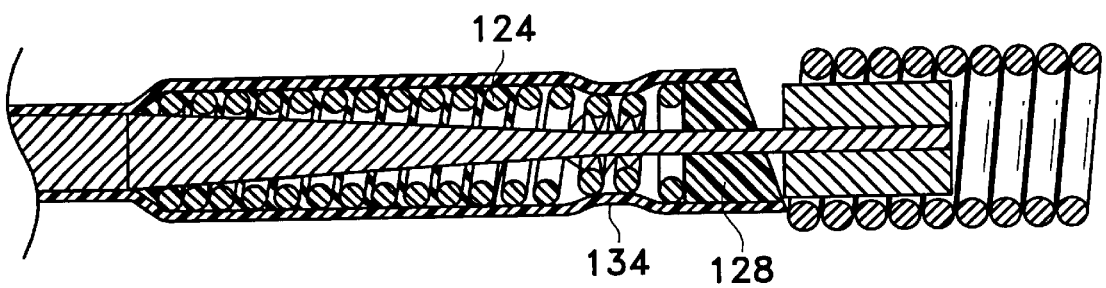
Figure 4:
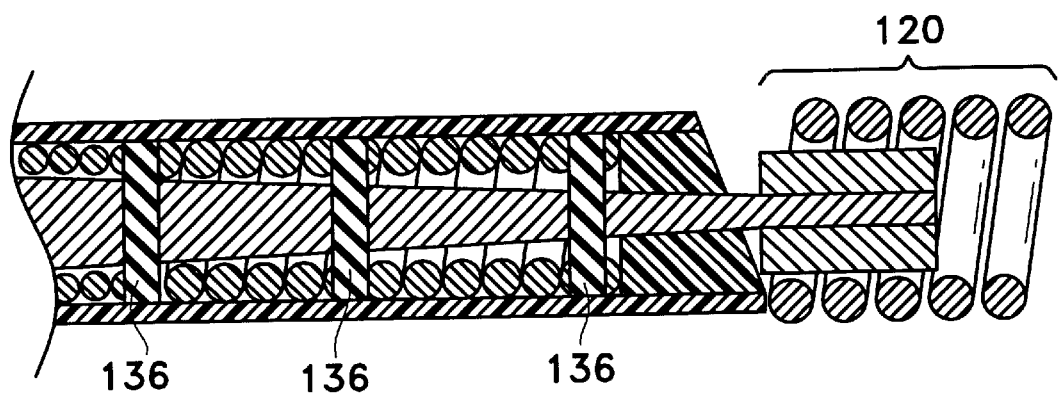

FIGS. 2–4 show variations of the distal portion of the core wire and manner in which it can be made strong and protected from incidental dissolution during electrolysis of the sacrificial joint 106 noted in the discussion of FIG. 1 above.

FIG. 2 again depicts the combination 120 of the detachable embolic device 102, the distal end of core wire 104, and the noble metal sleeve 108. More proximal to the dissolution area 106 is the assembly 122 making up the distal portion of core wire 104. Here, core wire 104 is shown to have a taper prior to reaching a region of constant diameter. The core wire 104 is surrounded by distal core coil 124 and marker coil 126. Distal coil 124 is placed for the purpose of providing column strength and flexibility to the distal section of the core wire assembly 122 in the region near the dissolution area 106. Marker coil 126 is placed to allow the attending physician, using a fluoroscope, to observe whether the core wire may be moved independently of the detachable embolic device assembly 120. If the core wire 104 is able to independently move, then dissolution of the sacrificial leg is complete. In this variation, core wire assembly 122 utilizes a bushing 128 which protects core wire 104 from contact with surrounding bodily fluid. The polymeric bushing 128, in addition to providing insulation for the core wire 104, is shown to have a distal surface which is cut at an angle to the axis of the core wire 104. This angle further delimits the area of the electrolytically sacrificial area 106 and additionally provides a lever to help with separation of the joint once it is broken through because of electrolysis. A castable polymer 130 is shown to be placed in the region between the proximal end of marker coil 126 and about halfway through the length of distal core coil 124. This cast or melted polymer, e.g., polyurethane, is used to secure the various coils in place without the use of solder. Finally, an outer polymeric covering 132 is shown on the outer periphery of distal core wire assembly 122. This outer covering 132 may be any of a variety of materials, but desirably is a slippery material such as a fluorocarbon, e.g., Teflon7. Other materials such as polyurethane or PET having a coating of a hydrophilic material of the type described in the prior art is also useful. A tight seal between the polymeric bushing 128 and the outer covering 132 helps assure that the core wire 104 sees a current only in the region desired.

FIG. 3 shows another variation of the joint depicted in FIG. 2, with the exception that a portion of coil 124 has been crimped and/or welded at a position 134 near the distal end of the coil. Again, this crimp and/or welding provides additional strength to the region of the core wire adjacent the polymeric bushing 128.

FIG. 4 depicts a further variation of the invention in which instead of the molten polymers described with regard to FIG. 2 or the crimping and welding described in conjunction with FIG. 3, the core wire is maintained in position using a glue or adhesive 136. These glues or adhesives may be any of a wide variety of known materials. For instance, they may be ultraviolet light curable polyacrylates or hot-melt adhesives or epoxies, to name just a few examples.

Figure 5:
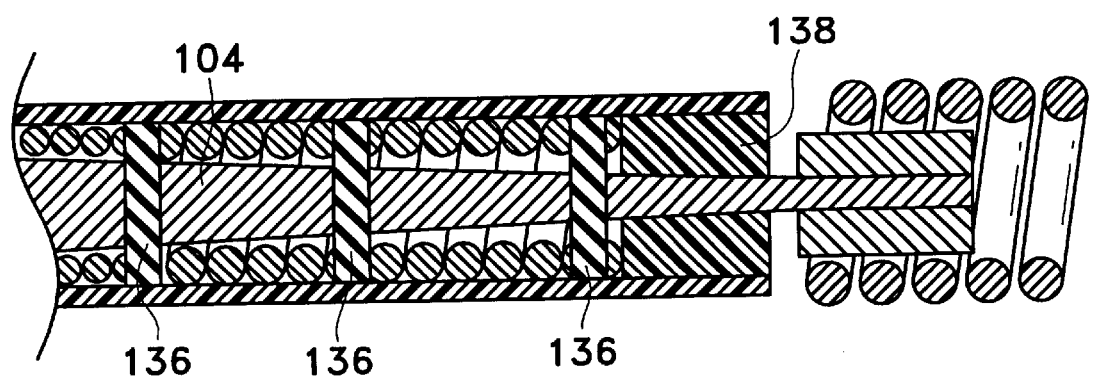

FIG. 5 shows a variation of the inventive joint using the glues or adhesives of (136) of FIG. 4 but depicting an insulator or more-noble metallic plug (138) sealing the core wire 104 against intrusion of surrounding fluid. In this instance, the plug 138 has a face which is generally perpendicular to the axis of the core wire 104. The shape of plug 138 is not particularly critical. A benefit has been noted for the slant cut plug or bushing shown in FIGS. 1, 2, 3 and 4, e.g., the slant cut provides a method for freeing the junction if difficulties with the junction are encountered. Nevertheless, each shape works well.

Figure 6:
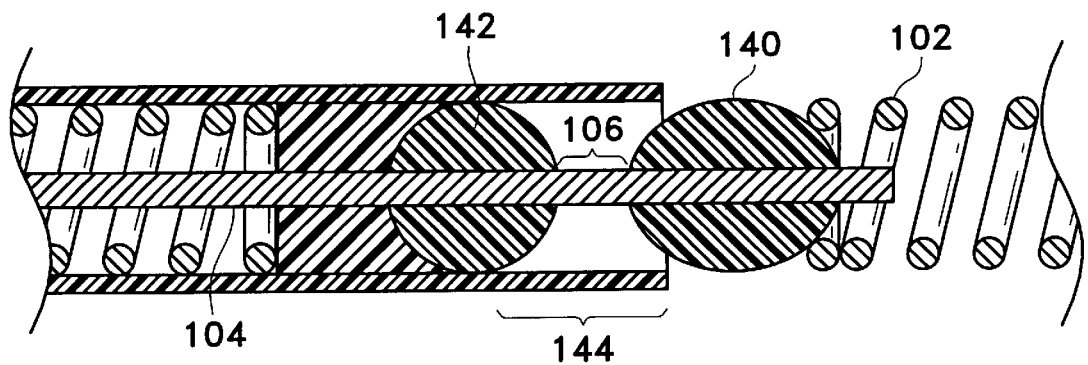

As a further indication of the invention described herein, FIG. 6 shows a variation using somewhat different shapes for the opposing features found on core wire 104 in which the area for electrolytic disintegration is housed to help assure the absence of any open projection from the electrolyzed joint. In this instance, however, a non-cylindrical attachment (140) has been attached to core wire. The depicted shape of bushing 140 is spherical but it may just as well be olive shaped or plug shaped or any other convenient size or shape which is able to be crimped and/or welded onto detachable embolic device 102. Similarly, opposite the sacrificial zone 106 on core wire 104 may be found bushing 142. Again, bushing 142 may be of a shape convenient for the designer of the device. The composition of bushings 140 and 142 may be either of an insulating material, e.g., a polymer, or of a metal more noble than that found in the bare core wire in the sacrificial region 106. In this variation, the sacrificial zone 106 is partially obscured by the presence of extension 144. Extension 144 is allowed to remain for the specific purpose of guarding the sacrificial zone 106 on the remote circumstance that a core wire, once electrolyzed, does not cleanly dissolve. We have not found this to be the case in using bushings which are welded and/or crimped to the core wire 104. It should be noted that in FIG. 6, bushing 140 is crimped onto core wire 104 and detachable vasoocclusive device 102 is welded onto the distal side of bushing 140.

Figure 7:
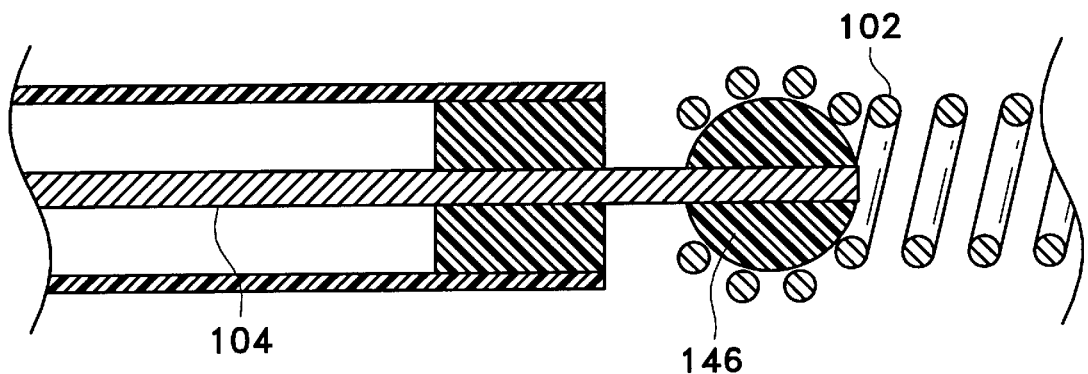

FIG. 7 shows a variation of the device shown in FIG. 6. Again, a detachable embolic device 102 is depicted. In this case, the detachable embolic device 102 is situated on the exterior surface of the bushing 146. The bushing is crimped and welded to core wire 104. The detachable embolic device 102 is welded onto the exterior of bushing 146. The more proximal portion of this device is similar to that shown, e.g., in FIGS. 1, 2 and 5. Again, the absence of solder provides for a clearly determinable and controllable time period for detachment of the vasoocclusive device 102.

Vasoocclusive device 102 is shown in each of the drawings above to be a coil. It may be a coil or a braid or other vasoocclusive device as is already known. The vasoocclusive device may be covered or connected with fibrous materials tied to the outside of the coil or braided onto the outer cover of the coil as desired. Such fibrous adjuvants may be found in U.S. Pat. No. 5,382,259 to Phelps et al., or in U.S. Pat. No. 5,226,911 to Chee et al., entitled "Vasoocclusion Coil with Attached Fibrous Elements", the entirety of which are incorporated by reference.

Furthermore, the releasable member 102 need not be a vasoocclusive device or a device to create emboli. The member may be any member suitable for detachment from the joint using electrolysis. These members may be, for instance, vena cava filters, vascular or bile duct stents, vaginally placed birth control devices, electrical activity monitoring leads, and any other device which my be either retained in place or later removed.

Figure 8:
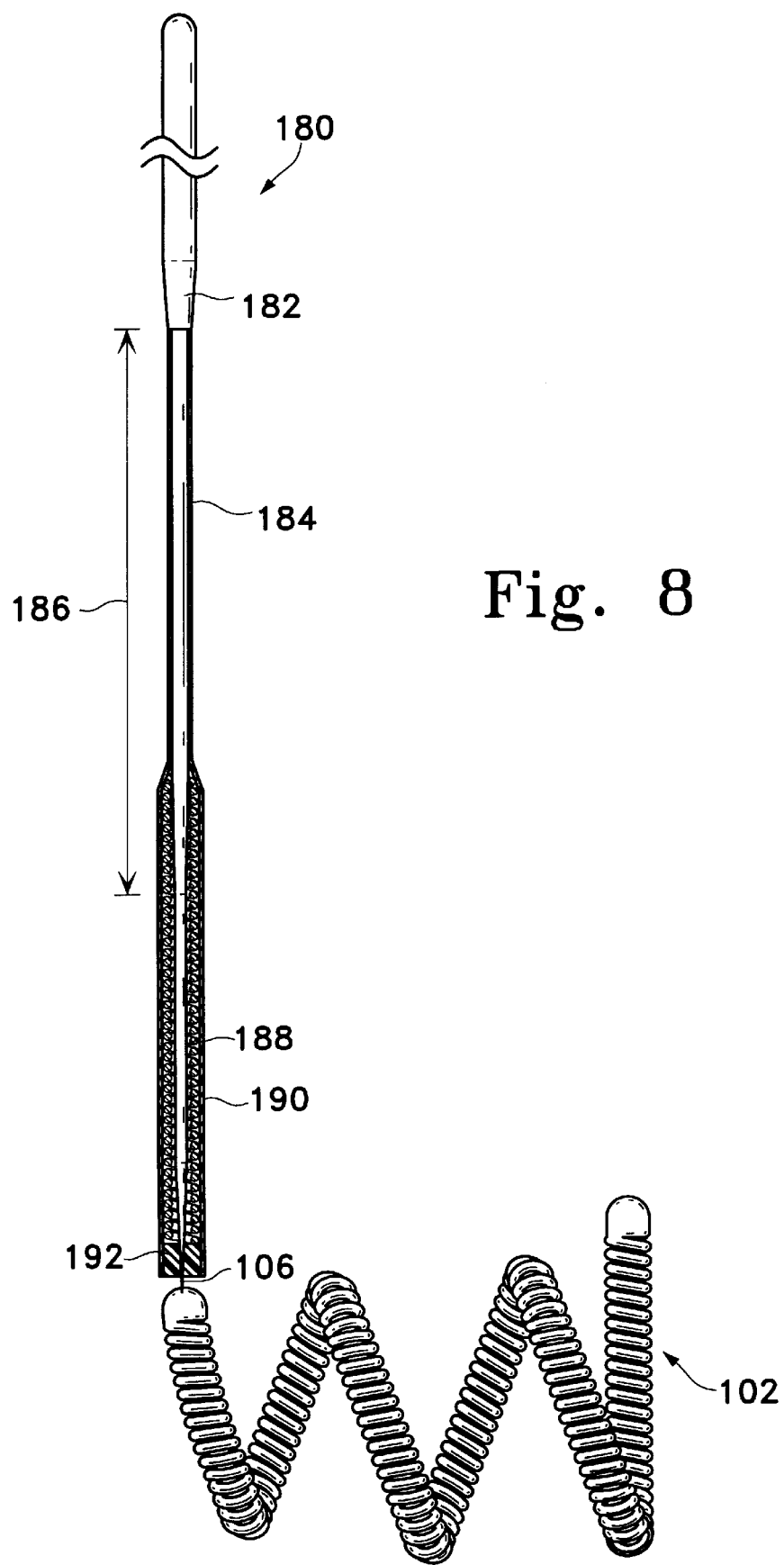
FIG. 8 shows side view of a typical assembly involving the inventive sacrificial link used in this invention.

FIG. 8 shows a typical layout involving the inventive discrete sacrificial region 106 as was generally shown in the Figures above. In FIG. 8, a somewhat conventional Teflon7 laminated or similarly insulated stainless steel core wire assembly 180 may be placed within a protective catheter. As was noted above, stainless steel core wire 180 may have a diameter of approximately 10–30 mils. In the noted embodiment in FIG. 8, core wire assembly 180 is tapered at its distal end to form a conical section 182 which joins a further section 184 which extends along a length of core wire 186. Section 184 then gradually narrows down to a thinner section 188. The core wire assembly 180, as noted above, may be placed within a catheter body and is typically 50–200 cm. in length down to sacrificial link 106. The distal section of core wire assembly 180 has an outer Teflon7 sleeve 190 (or sleeve of other appropriate insulating material). Furthermore, it has an end plug 192 to permit isolation of the guidewire electrically from the blood except at sacrificial discrete link 106. The proximal end of vasoocclusive device 102 is typically a soldered tip or ajoint. Preferably, vasoocclusive device 102, when a coil, forms a secondary loop after it emanates from the end of the catheter. The distal end of vasoocclusive device 102 may also have an end plug or tip to prevent punctures of the aneurysm when introduced into the aneurysm sac.

As noted, the detachable member (e.g., a coil or vasoocclusive device) 102 may be pre-biased to form a cylinder or conical envelope. However, the vasoocclusive device 102 is extremely soft and its overall shape is easily deformed. When inserted within the catheter (not shown), the vasoocclusive device 102 is easily straightened so to lie axially within the catheter. Once ejected from the tip of the catheter, vasoocclusive device 102 may form a shape shown in FIG. 8 or may be loosely deformed to conform to the interior shape of the aneurysm.

Figure 9:
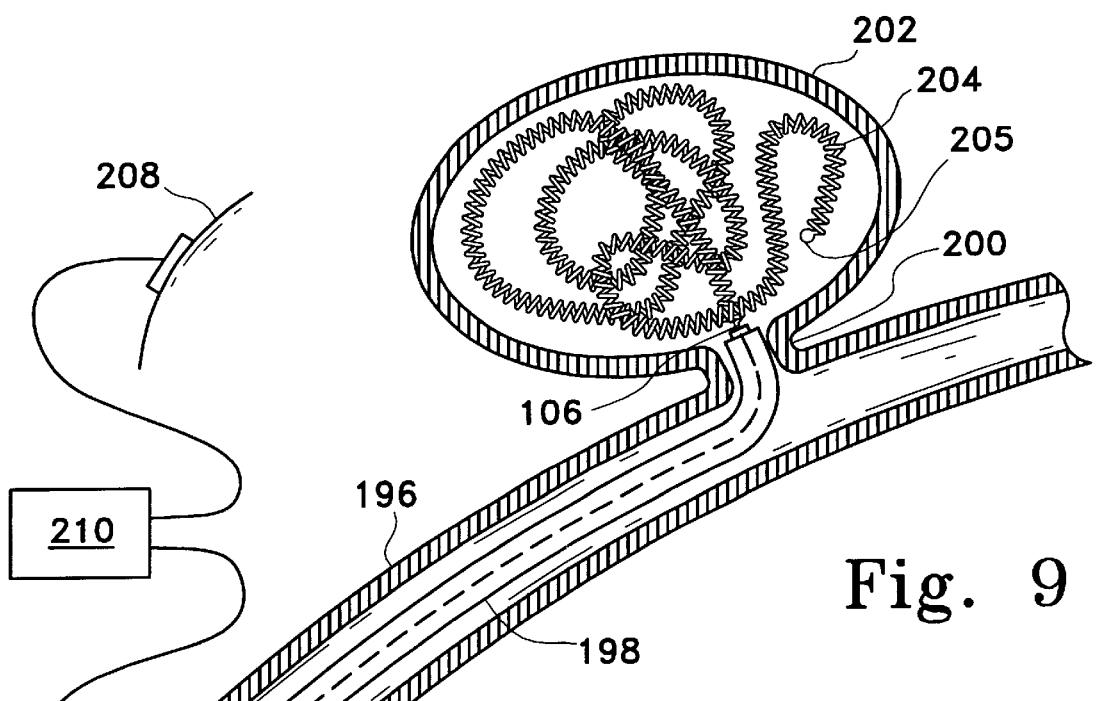
FIGS. 9 and 10 schematically depict the method for deploying the vasoocclusive device using the inventive sacrificial link.

FIG. 9 shows the placement of the inventive devices shown above within a vessel 196 with the tip of catheter 198 placed near neck 200 of aneurysm 202. Vasoocclusive device 204 is fed into aneurysm 202 at least until sacrificial link 106 is exposed beyond the distal tip of the catheter 198. A positive electric current of approximately 0.01–2 milliamps at 0.1–6 volts is applied to core wire 206 to form a thrombus within aneurysm 202. The negative pole 208 of power supply 210 is typically placed in electrical contact with the skin. It is also desirable that the current be allowed to return through a conductor placed in the wall of the catheter (or the guide catheter used in conjunction with the catheter).

After the thrombus has been formed and the aneurysm occluded, vasoocclusive device 204 is detached from core wire 206 by electrolytic disintegration of sacrificial link 106.

Figure 10:
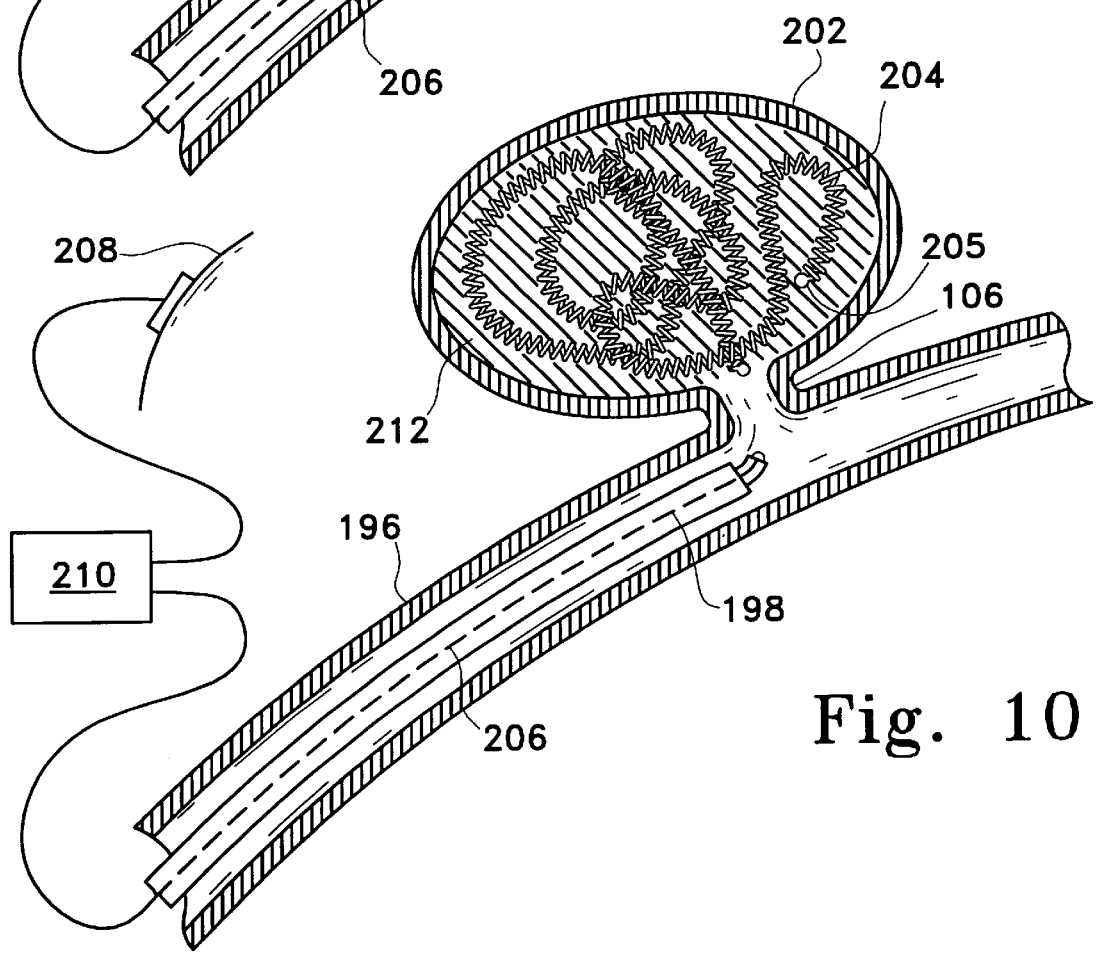

After sacrificial link 106 is completely dissolved by electrolytic action, typically within 5 seconds to 5 minutes, the core wire 206 and catheter 196, are removed from the vessel, leaving aneurysm 202 occluded 212 as shown in FIG. 10.

The process is typically practiced under fluoroscopic control with local anesthesia. A transfemoral catheter is utilized to treat a cerebral aneurysm and is usually introduced at the groin. When the vasoocclusive device 204 is platinum, it is not affected by electrolysis. When the core wire and pertinent portions of the supporting coils at the distal tip of the guidewire are adequately coated with insulating coverings, only the exposed portion at the sacrificial link 106 is affected by the electrolysis.

Procedures for using this invention in non-vascular systems of the body are carried out in a similar fashion. The chosen site must be accessible and the site must provide a local medium of sufficient ionic nature to allow electrolysis of the sacrificial joint to take place.

Many alterations and modifications may be made by those having ordinary skill in the art without departing from the spirit and scope of the invention. Therefore, it must be understood that the shape of the distal tip or distal platinum coil used in combination with the core wire according to the invention may be provided with a variety of shapes and envelopes.

EXAMPLE

Ten examples of the joint depicted in FIG. 3 were produced. The core wire was 0.003" at the sacrificial joint, the joint was 0.005" in length. The distal bushing was a platinum alloy. Each of the examples was introduced into a saline solution and a voltage of 3.0 v at 1.0 ma was applied to the junction. The junction dissolved in a short period of time—each between 44 seconds and 97 seconds.

The illustrated embodiments have been used only for the purposes of clarity and should not be taken as limiting the invention as defined by the following claims.

We claim as our invention:

1. A mammalian implant assembly comprising:
   a wire having an axis, a proximal end, and a distal end, a distal portion of the wire comprising a discrete metallic link that is susceptible to electrolytic disintegration in an ionic medium, a section of the wire proximal of said link being insulated so as to not be susceptible to electrolytic disintegration in the ionic medium; and
   a detachable implant coupled to the wire by a solder-less attachment at a location that is distal to the discrete metallic link, the implant comprised of a material not susceptible to electrolytic disintegration in an ionic medium.

2. The assembly of claim 1 where the distal end of the wire has a constant diameter.

3. The assembly of claim 1 additionally comprising means for providing column strength to the distal section of the wire.

4. The assembly of claim 1, wherein the distal end of the wire is tapered.

5. A mammalian implant assembly, comprising:
   a wire having an axis, a proximal end, and a distal end, a distal portion of the wire comprising a discrete metallic link that is susceptible to electrolytic disintegration in an ionic medium, a section of the wire proximal of said link being insulated so as to not be susceptible to electrolytic disintegration in the ionic medium;
   a detachable implant joined to the wire without solder, the implant comprised of a material not susceptible to electrolytic disintegration in an ionic medium; and
   a sleeve comprised of a material not susceptible to electrolytic disintegration in an ionic medium, the sleeve joining the wire to the implant.

6. The assembly of claim 5 where the sleeve is metallic.

7. The assembly of claim 5, wherein the detachable implant is welded to the sleeve.

8. The assembly of claim 5, wherein the detachable implant is crimped onto the sleeve.

* * * * *